US006362145B1

(12) United States Patent
Littau et al.

(10) Patent No.: US 6,362,145 B1
(45) Date of Patent: Mar. 26, 2002

(54) CLEAR SOAP BAR COMPRISING METAL CATALYST SODIUM COCOYL ISETHIONATE

(75) Inventors: Cheryl A. Littau; Linda Talley Wilhelm, both of Charlotte, NC (US)

(73) Assignee: Clariant International Ltd., Muttenz (CH)

(*) Notice: Subject to any disclaimer, the term of this patent is extended or adjusted under 35 U.S.C. 154(b) by 0 days.

(21) Appl. No.: 09/712,112

(22) Filed: Nov. 14, 2000

(51) Int. Cl.[7] .................................................. A61K 7/50

(52) U.S. Cl. ....................... 510/147; 510/152; 510/153; 510/155; 510/156

(58) Field of Search ................................ 510/147, 151, 510/152, 155, 156, 153

(56) References Cited

U.S. PATENT DOCUMENTS

| | | | | | |
|---|---|---|---|---|---|
| 1,881,172 | A | | 10/1932 | Daimler et al. | |
| 2,303,582 | A | | 12/1942 | Russell et al. | |
| 2,307,953 | A | | 1/1943 | Potter | |
| 2,316,719 | A | | 4/1943 | Russell | |
| 2,328,931 | A | | 9/1943 | Steik | |
| 2,635,103 | A | | 4/1953 | Molteni et al. | |
| 2,806,044 | A | | 9/1957 | Weil et al. | |
| 2,821,535 | A | | 1/1958 | Britton et al. | |
| 2,857,370 | A | | 10/1958 | Sundberg | |
| 2,863,887 | A | | 12/1958 | Becher | |
| 2,898,352 | A | | 8/1959 | Schenck | |
| 2,923,724 | A | | 2/1960 | Anderson et al. | |
| 3,004,049 | A | | 10/1961 | Schenck | |
| 3,029,264 | A | | 4/1962 | Alphen et al. | |
| 3,150,156 | A | | 9/1964 | Lamberti | |
| 3,151,156 | A | | 9/1964 | Marten et al. | |
| 3,167,570 | A | | 1/1965 | Bohunek | |
| 3,320,292 | A | | 5/1967 | Cahn et al. | |
| 3,383,396 | A | | 5/1968 | Cahn et al. | |
| 3,394,155 | A | | 7/1968 | Cahn et al. | |
| 3,420,857 | A | | 1/1969 | Holland et al. | |
| 3,420,858 | A | | 1/1969 | McCrimlisk | |
| 3,429,136 | A | | 2/1969 | Holt et al. | |
| 3,745,181 | A | | 7/1973 | Wrigley et al. | |
| 3,880,897 | A | | 4/1975 | Landy | |
| 3,997,576 | A | | 12/1976 | Oghoshi et al. | |
| 4,092,259 | A | | 5/1978 | Prince | |
| 4,096,082 | A | | 6/1978 | Prince | |
| 4,100,097 | A | | 7/1978 | O'Roark | |
| 4,151,105 | A | | 4/1979 | O'Roark | |
| 4,352,759 | A | | 10/1982 | Schwarte | |
| 4,369,144 | A | | 1/1983 | Lamberti et al. | |
| 4,405,526 | A | | 9/1983 | Lamberti et al. | |
| 4,476,055 | A | | 10/1984 | Du Vernet | |
| 4,515,721 | A | | 5/1985 | Login et al. | |
| 4,536,338 | A | | 8/1985 | Urban et al. | |
| 4,537,724 | A | | 8/1985 | McKinnie et al. | |
| 4,851,147 | A | * | 7/1989 | Esposito et al. | 252/108 |
| 5,041,233 | A | | 8/1991 | Kutny et al. | |
| 5,069,828 | A | | 12/1991 | Dumas et al. | |
| 5,154,849 | A | * | 10/1992 | Visscher et al. | 252/174.15 |
| 5,300,665 | A | | 4/1994 | Tracy et al. | |
| 5,384,421 | A | | 1/1995 | Day et al. | |
| 5,393,466 | A | | 2/1995 | Ilardi et al. | |
| 5,434,276 | A | | 7/1995 | Walele et al. | |
| 5,496,488 | A | * | 3/1996 | Kacher et al. | 252/125 |
| 5,496,959 | A | | 3/1996 | Day | |
| 5,523,432 | A | | 6/1996 | Raths et al. | |
| 6,069,262 | A | | 5/2000 | Walele et al. | |

* cited by examiner

*Primary Examiner*—Necholus Ogden
(74) *Attorney, Agent, or Firm*—Anthony A. Bisulca

(57) ABSTRACT

A clear soap bar formulation based on sodium cocoyl isethionate (SCI) and method for producing a clear soap bar. The soap bar formulation uses a SCI prepared with metal catalyst (for example zinc) to promote faster and more economical production of SCI. The clear soap bar is formed from a preliminary mixture of propylene glycol, sorbitol, sodium lauryl ether sulfate (SLES), glycerin, water, stearic acid and myristic acid. Sodium hydroxide is added for saponification of the fatty acids to form soap. The resulting mixture is stirred until homogeneous, and a chelating agent is added. The mixture is stirred again until homogeneous. SCI is then added, and the mixture is stirred until substantially clear. The mixture is then allowed to sit without stirring for a period of time, in order to allow air bubbles to rise to the top of the vessel. The mixture is poured into molds and allowed to cool undisturbed. The clear soap bar formulation may also contain one or more common soap bar ancillary agents including but not limited to foam stabilizers, humectants, emollients, fragrances, and chelating agents.

20 Claims, No Drawings

CLEAR SOAP BAR COMPRISING METAL CATALYST SODIUM COCOYL ISETHIONATE

FIELD OF THE INVENTION

The present invention relates generally to soap bars and, more particularly, to production of clear soap bars prepared from sodium cocoyl isethionate.

BACKGROUND OF THE INVENTION

Soaps have been traditionally prepared from fatty acids, such as tallow class fats, that have surface-active agent, or surfactant, qualities, namely simultaneous solubility in both aqueous and organic phases. This dual nature allows surfactants to clean dirt and oil from surfaces and produce lather. The primary surfactants used in soap bars are sodium salts of fatty acids.

Formulation of bar soaps have become increasingly complicated because of changes in bathing habits of consumers and emphasis on marketability of bar soaps to such customers. For example, because consumers bathe more frequently than in the past, milder soaps have been formulated. Performance of bar soaps are measured by lather, wet cracking, firmness and rinsability in addition to mildness to skin. To improve the performance of bar soaps and provide additional consumer benefits, a variety of additives may be formulated into soap bars including free fatty acids, glycerol, colorants, dyes, pigments, fragrance, chelants, antioxidants, mildness and skin additives, antimicrobial agents and synthetic surfactants.

Synthetic surfactants commonly have lower sensitivity to water hardness which results in a bar soap formulation having improved rinsing, lathering and general "feel to skin". Anionic class surfactants, such as sodium cocoyl isethionate (SCI), are commonly used synthetic surfactants in bar soap formulation. SCI is a milder surfactant but soap bars incorporating SCI typically cost more than simple soaps.

Recently, clear or transparent soap bars have become increasingly popular among consumers. For example, clear soap bars are aesthetically pleasing to a consumer's eyes while also providing cleansing properties commonly associated with opaque or translucent soap bars. Clear soap bars have been prepared from SCI, but only SCI that had been prepared using an organic acid catalyst yielded bars of good clarity. Use of organic acid catalysts can be problematic in the production of SCI, leading to either longer reaction times or lower activity levels than those achievable with inorganic catalysts, making the SCI more expensive on a per pound active basis.

What is therefore needed is a clear soap bar that can be prepared from SCI that contains/is produced using inorganic catalysts which is more economical and faster than SCI produced using organic acid catalysts. Further needed is a clear soap bar formulation based on metal catalyzed SCI and method of producing the clear soap bar.

SUMMARY OF THE INVENTION

The present invention is a clear soap bar formulation based on sodium cocoyl isethionate (SCI) and method for producing the clear soap bar. The invented soap bar formulation uses a SCI prepared with zinc catalyst to promote faster and more economical production of SCI. In a preferred embodiment, tetrasodium ethylene diaminetetraacetic acid (EDTA) is added to the soap bar formulation, depending on the zinc content of the formulation, to eliminate opacity and produce a substantially clear soap bar. Addition of EDTA to the soap bar formulation at a ratio to zinc content is preferably from about 1:1 to about 5:1 by weight. The invented clear soap bar formulation may also contain one or more common soap bar ancillary agents including but not limited to foam stabilizers, humectants, emollients, and fragrances.

In one embodiment, the invented clear soap bar is formed from a preliminary mixture of propylene glycol, sorbitol, sodium lauryl ether sulfate (SLES), glycerin, water, stearic acid and myristic acid. The preliminary mixture is stirred and heated, and sodium hydroxide is added for saponification of the fatty acids to form soap. The resulting mixture is stirred until homogeneous, and EDTA is added. The mixture is stirred again until homogeneous. SCI is then added, and the mixture is stirred until substantially clear. The mixture is then allowed to sit without stirring for a period of time, in order to allow air bubbles to rise to the top of the vessel. The mixture is poured into molds and allowed to cool undisturbed.

The method for producing the clear soap bar includes the steps of: producing a mixture of propylene glycol, sorbitol, SLES, glycerin, water, stearic acid and myristic acid in a vessel; heating the mixture while stirring to a temperature from about 45° C. to about 65° C.; when the mixture is completely molten, slowly adding NaOH while maintaining a temperature of the mixture from bout 65° C. to about 75° C.; stirring the mixture until it is substantially homogenized; adding EDTA to the mixture at a quantity based on the zinc content of the SCI of about 1:1 to about 5:1 by weight; stirring the mixture until the mixture is substantially homogenized; adding SCI and stirring until the mixture is substantially homogenized and the SCI is dissolved at a temperature from about 65° C. to about 75° C. and stirring for about 60 minutes to about 120 minutes; allowing air bubbles in the mixture to rise to the surface; pouring the mixture into molds at a temperature from about 65° C. to about 75° C.; and, cooling the mixture undisturbed.

DETAILED DESCRIPTION OF THE INVENTION

The present invention is a clear soap bar based on sodium cocoyl isethionate (SCI) that is more economical to produce and is processed faster than conventional soap bars based on SCI. Further, the present invention is a clear soap bar based on SCI where the SCI does not require production from an organic catalyst. The invented clear soap bar is milder than traditional soap and can be used on a regular basis by individuals. The invented clear soap bar includes a primary mixture of propylene glycol, sorbitol, an anionic surfactant, glycerin, water, stearic acid and myristic acid. Sodium hydroxide, a chelating agent, and SCI are added to the primary mixture in accordance with the invented process described in greater detail hereinafter.

The clear soap bar formulation may optionally include common soap bar ancillary agents including but not limited to foam stabilizers, humectants, emollients, antibacterial agents and fragrances. Examples of foam stabilizers include alkyl monoethanolamides, alkyl diethanolamides, acyl sarcosinates, acyl taurates, acyl isethionates, acyl lactates, alkyl amine oxides, alkyl betaines, alkyl ether carboxylates, acyl glutamates and mixtures thereof. Examples of humectants include glycerine, propylene glycol, butylene glycol, polyethylene glycol and mixtures thereof. Examples of emollients include mineral oil, vegetable oil, silicone oils, synthetic and semisynthetic emollient esters and mixtures thereof.

Ethylene diaminetetraacetic acid (EDTA) is preferably used as a chelating agent. Examples of alternative chelating agents include pentasodium diethylenetriamine pentaacetic acid (DTPA), sodium etidronate (EDHP) and citric acid. The clear soap bar may further include mildness and skin additives such as lanolin, vitamin E, aloe vera gel, and panthenol.

In one embodiment, the invented clear soap bar is formed from a preliminary mixture of propylene glycol, sorbitol, an anionic surfactant such as sodium lauryl ethyl sulfate (SLES), glycerin, water, stearic acid and myristic acid. The preliminary mixture is mixed and heated, and sodium hydroxide is added for saponification of the fatty acids to form soap. The resulting mixture is stirred until homogeneous, and a chelating agent, such as EDTA, is added. The mixture is stirred again until homogeneous. SCI is then added, the mixture is stirred for a period until the mixture is substantially clear with an additional period from about 1 to about 2 hours before stirring is ceased, and the mixture is allowed to settle. The processed mixture is poured into molds and cooled undisturbed.

The following Table I is a preferred embodiment of components and amounts of the present invention:

In a preferred embodiment, all components of A are mixed in a vessel and heated to a temperature from about 45° C. to about 65° C. When the acids of component A are completely molten, NaOH is added very slowly, such as dropwise, to the mixture to control the exotherm during saponification to preferably at or below 70° C.±5° C. The mixture is mixed well at this temperature until homogeneous, and preferably mixed for about 30 minutes. EDTA is then added and the mixture is stirred for a few minutes until substantially homogeneous. SCI 85 is then added. The mixture is stirred until substantially clear at a temperature of about 70° C.±5° C.; preferably for about 30 minutes when using powdered SCI 85 or about 60 minutes when using chip type SCI 85. Sodium Laureth-13-Carboxylate (Sandopan® LS24N) (D) is then added. The mixture is stirred until the mixture is homogenized. TEA (E) is then added and the mixture is stirred for a period of about 60 to about 120 minutes. The stirrer is turned off and air bubbles are allowed to rise to top of flask for a period of about 30 minutes. Then, the mixture is poured into molds at a temperature of about 70° C.±5° C. The bars are allowed to cool undisturbed. When cooled, the bars are removed from the molds and wrapped.

In the aforementioned stirring after the addition of TEA, extended stir times at high temperature tend to discolor the final bars, and too short of a stir time yields bars that are slightly hazy. A two-hour stir after all ingredients have been added is sufficient to achieve the clarity desired without discoloration of the mixture under air. Chelating agents may be selected from the list including but not limited to ethylenediaminetetraacetic acid, disodium salt dihydrate, diammonium salt of ethylenediaminetetraacetic acid, Ethylenetriaminepentaacetic acid, DeQuest 2066 (AS# 22042-96-2), also known as phosphonic acid, [(phosphonomethyl)imino] bis[(2,1-ethanediylnitrilo) tetrakis(methylene)]tetrakis-sodium salt, and DTPA.

TABLE 1

Formulation And Preferred Ranges (percentage by weight composition)

| | Ingredient | Full Range | Preferred Range | More Preferred Range | Most Preferred Range |
|---|---|---|---|---|---|
| A | Propylene Glycol | 8.0–22.0% | 10.0–20.0% | 12.0–18.0% | 14.0–16.0% |
| | Sorbitol (70%) | 8.0–16.0% | 10.0–15.0% | 11.0–14.0% | 12.0–13.0% |
| | SLES (60%, W/EtOH) | 16.0–27.0% | 18.0–25.0% | 19.0–23.0% | 20.0–21 .0% |
| | Glycerin | 10.0–15.0% | 11.0–14.0% | 12.0–14.0% | 13.0–14.0% |
| | Water | 2.0–4.0% | 2.0–4.0% | 3.0–4.0% | 3.0–4.0% |
| | Stearic Acid | 13.0–15.0% | 13.0–15.0% | 14.0–15.0% | 14.0–15.0% |
| | Myristic Acid | 6.0–7.0% | 6.0–7.0% | 6.0–7.0% | 6.0–7.0% |
| B | Sodium Hydroxide (50%) | 6.0–7.0% | 6.0–7.0% | 6.0–7.0% | 6.0–7.0% |
| G | EDTA | 0.10–1% | 0.10–0.8% | 0.10–0.5% | 0.2–0.3% |
| D | Hostapon ® SCI 85 | 3.0–6.0% | 3.0–5.5% | 3.0–5.5% | 4.0–5.0% |
| | Sandopan ®LS24N | 0–5.0% | 0–4.5% | 0–4.0% | 0–3.5% |
| E | TEA or Ammonium Hydroxide | 0–1.5% | 0–1.25% | 0–1.0% | 0–1.0% |

The method for producing the clear soap bar includes the steps of: producing a soap bar mixture of propylene glycol, sorbitol, an anionic surfactant such as SLES, glycerin, water, stearic acid and myristic acid (Table 1, component A) in a vessel; heating the mixture while stirring to a temperature from about 45° C. to about 65° C.; when the mixture is completely molten, slowly adding NaOH (Table 1, component B) while maintaining a temperature of the mixture from about 65° C. to about 75° C.; stirring until the mixture is substantially homogenized; adding EDTA (Table 1, component C) to the mixture at a quantity of about 1:1 to about 5:1 by weight based on the quantity of metal catalyst (e.g., zinc content) in SCI; stirring the mixture until the mixture is substantially homogenized; adding SCI (Hostapon® SCI 85 manufactured by Clariant Corporation, Charlotte, N.C.) (Table 1, component D) and stirring until the mixture is substantially clear and homogenized and the SCI is dissolved at a temperature from about 65° C. to about 75° C.; adding sodium laureth-13-carboxylate (Sandopan® LS24N manufactured by Clariant Corporation, Charlotte, N.C. (Table 1, component D) and stirring until the mixture is homogenized; adding triethanol amine (TEA) (Table 1, component E) and stirring for about 60 minutes to about 120 minutes; stopping agitation and allowing air bubbles in the mixture to rise to the surface; pouring the mixture into molds at a temperature from about 65° C. to about 75° C.; and, cooling the mixture undisturbed.

Alternative components include mild surfactants such as alkyl ether carboxylates, acyl glutamates, and amphoacetates. Ammonium hydroxide may be substituted for TEA. Other additives that are normal and customary for conventional soap bars may also be added to the soap bar mixture including but not limited to preservatives, dye, fragrance, vitamins (e.g., Vitamin E), botanical extracts, panthenol, and conditioning polymers.

EXAMPLES

Example 1

Hostapon® SCI 85 with no EDTA

Example 1 demonstrates what results are achieved in a produced soap bar without the use of a chelating agent at levels in the range from 1:1 to 5:1 by weight based on the catalyst content in the SCI. Weigh the following ingredients directly into a 1 liter reaction flask using a laboratory analytical balance:

| | |
|---|---|
| Propylene Glycol | 200 grams |
| Sorbitol (70%) | 150 grams |
| SLES (60%, w/EtOH) | 175 grams |
| Glycerin | 135 grams |
| Water | 27 grams |
| Stearic Acid | 130 grams |
| Myristic Acid | 60 grams |

Setup the flask with a heat jacket and stirrer. Seal the flask to minimize water loss during the process. Operate the stirrer on high and heat the flask to 59° C. When the acids are molten, begin a very slow/dropwise addition of 60 grams of sodium hydroxide (50%), to control the exotherm during saponification at or below 70° C. Mix well at this temperature until homogeneous (approximately 30 minutes), then add 50 grams of SCI 85 powder and stir approximately 30 minutes until mixture is clear at 70° C. Add 10 grams of TEA and stir 60 minutes. Turn off stirrer and let air rise to the top of flask (about 30 minutes), then pour into bar molds at 70° C. Allow bars to cool undisturbed. When cooled, remove the bars from molds and wrap. The resulting cooled bars were not clear but also were not 100% opaque.

Example 2

Hostapon® SCI 85 with EDTA

Example 2 shows how the addition of a chelating agent in a sufficient quantity helps to clarify the produced soap bar. Weigh the following ingredients directly into a 1 liter reaction flask using a laboratory analytical balance:

| | |
|---|---|
| Propylene Glycol | 200 grams |
| Sorbitol (70%) | 150 grams |
| SLES (60%, w/EtOH) | 175 grams |
| Glycerin | 135 grams |
| Water | 27 grams |
| Stearic Acid | 130 grams |
| Myristic Acid | 60 grams |

Setup the flask with a heat jacket and stirrer. Seal the flask to minimize water loss during the process. Operate the stirrer on high and heat to 59° C. When the acids are molten, begin a very slow/dropwise addition of 60 grams of sodium hydroxide (50%), to control the exotherm during saponification at or below 70° C. Mix well at this temperature until homogeneous, (approximately 30 minutes), then add 3 grams EDTA. Mix for a few minutes to homogenize the mixture again, then add 50 grams of SCI 85 powder and stir approximately 30 minutes until the mixture is completely clear at 70° C. Add 10 grams of TEA and stir for about 60 minutes. Turn off the stirrer and let air rise to top of flask (about 30 minutes), then pour into bar molds at 70° C. Allow bars to cool undisturbed. When cooled, remove the bars from molds and wrap. The resulting cooled bars were clear.

Example 3

Hostapon® SCI 85 with EDTA in combination with Sandopan® LS24N

Example 3 shows how the addition of a chelating agent in a sufficient quantity helps to clarify the produced soap bar. Weigh the following ingredients directly into a 1 liter reaction flask using a laboratory analytical balance:

| | |
|---|---|
| Propylene Glycol | 180 grams |
| Sorbitol (70%) | 120 grams |
| SLES (60% w/EtOH) | 205 grams |
| Vitamin E | 1.0 grams |
| Jojoba Oil | 2.5 grams |
| Panthenol | 1.0 grams |
| Glycerin | 120 grams |
| Water | 31.5 grams |
| Stearic Acid | 130 grams |
| Myristic Acid | 60 grams |

Setup the flask with a heat jacket and stirrer. Seal the flask to minimize water loss during the process. Operate the stirrer on high and heat to 59° C. When the acids are molten, begin a very slow/dropwise addition of 60 grams of sodium hydroxide (50%), to control the exotherm during saponification at or below 70° C. Mix well at this temperature until homogeneous, (approximately 30 minutes), then add 4 grams EDTA. Mix for a few minutes to homogenize again, then add 50 grams of SCI 85 powder and stir until the mixture is sufficiently clear at 70° C. Add 35 grams of Sandopan® LS24N and stir for about 90 minutes. Turn off the stirrer and let air rise to top of flask (about 30 minutes), then pour into bar molds at 70° C. Allow bars to cool undisturbed. When cooled, remove the bars from molds and wrap. The resulting cooled bars were clear.

Example 4

Sandopan® LS24N with and without EDTA

Example 4 demonstrates that the addition of a sufficient amount of EDTA has beneficial effects on the produced soap bars without adding Hostapon® SCI 85. Duplicate reaction flasks were setup. Weigh the following ingredients directly into each of the 1 liter reaction flask using a laboratory analytical balance:

| | |
|---|---|
| Propylene Glycol | 200 grams |
| Sorbitol (70%) | 150 grams |
| SLES (60%, w/EtOH) | 175 grams |
| Glycerin | 135 grams |
| Water | 27 grams |
| Stearic Acid | 130 grams |
| Myristic Acid | 60 grams |

Setup each of the flasks with a heat jacket and stirrer. Seal the flasks to prevent water loss during the process. Turn the stirrer of each flask to high and heat to 59° C. When acids in each flask are molten, begin a very slow/dropwise addition of 60 grams of sodium hydroxide (50%), to control the exotherm during saponification to preferably at or below 70° C. Mix well at this temperature until homogeneous (approximately 30 minutes), then add 3 grams of EDTA to one of the flasks. Continue to mix both flasks for a few minutes so that the flask with the EDTA has a chance to homogenize again, then add 50 grams of Sandopan® LS24N to each of the two flasks and stir approximately 30 minutes until the mixture is completely clear at 70° C. Add 10 grams of TEA to each of the two flasks and stir 60 minutes. Turn off the stirrers and let air rise to top of flasks (30 minutes), then pour into molds at 70° C. Allow bars to cool undisturbed. When cooled, remove the bars from molds and wrap. Cooled bars were clear, but the degree of clarity was improved by the addition of the EDTA.

The foregoing description of the specific embodiments will so fully reveal the general nature of the invention that others can, by applying current knowledge, readily modify and/or adapt for various applications such specific embodiments without departing from the generic concept and, therefore, such adaptations and modifications should and are intended to be comprehended within the meaning and range of equivalents of the disclosed embodiments.

It is to be understood that the phraseology or terminology employed herein is for the purpose of description and not of limitation. Accordingly, the invention is intended to embrace all such alternatives, modifications, equivalents and variations as fall within the spirit and broad scope of the appended claims.

What is claimed is:

1. A clear soap bar composition comprising:

a primary mixture comprising: propylene glycol; sorbitol; a first anionic surfactant; glycerin; water; stearic acid; and myristic acid;

sodium hydroxide;

a second anionic surfactant, wherein said second anionic surfactant sodium cocoyl isethionate (SCI); and a chelating agent in sufficient quantity to be in the range of about 1:1 to about 5:1 by weight based on the quantity of metal catalyst present in said SCI.

2. A clear bar soap composition according to claim 1 wherein said chelating agent is selected from ethylenediaminetetraacetic acid (EDTA), disodium salt dihydrate, diammonium salt of ethylenediaminetetraacetic acid, tetrasodium ethylene diaminetetraacetic acid, ethylenetriaminepentaacetic acid, phosphonic acid,[(phosphonomethyl)imino]bis[(2,1-ethanediylnitrilo)tetrakis(methylene)] tetrakis-sodium salt, and pentasodium diethylenetriamine pentaacetic acid (DTPA).

3. A clear soap bar composition according to claim 1 wherein said first anionic surfactant is selected from sodium lauryl ether sulfate (SLES), alkyl ether carboxylate, acyl glutamate, amphoacetate, and a combination thereof.

4. A clear bar soap composition according to claim 1 wherein said propylene glycol is from about 8 to about 22% by weight of said composition, said sorbitol is from about 8 to about 16% by weight of said composition, said first anionic surfactant is from about 16 to about 32% by weight of said composition, said glycerin is from about 10 to about 15% by weight of said composition, said water is from about 2 to about 4% by weight of said composition, said stearic acid is from about 13 to about 15% by weight of said composition, said myristic acid is from about 6 to about 7% by weight of said composition, said sodium hydroxide is from about 6 to about 7% by weight of said composition, said chelating agent is from about 0.1 to about 1% by weight of said composition, and said SCI is from about 3 to about 6% by weight of said composition.

5. A clear bar soap composition according to claim 1 further comprising at least one additive selected from a preservative, a dye, a fragrance, a vitamin, a botanical extract, panthenol, a conditioning polymer, a foam stabilizer, a humectant, and an emollient.

6. A clear bar soap composition comprising:

a primary mixture comprising: propylene glycol; sorbitol; a first anionic surfactant; glycerin; water; stearic acid; and myristic acid;

sodium hydroxide;

a second anionic surfactant, wherein said second anionic surfactant is sodium cocoyl isethionate (SCI);

a chelating agent in sufficient quantity to be in the range of about 1:1 to about 5:1 by weight based on the quantity of metal catalyst present in said SCI; and one of triethanol amine (TEA) and ammonium hydroxide;

wherein said SCI is a zinc catalyst prepared SCI.

7. A clear bar soap composition according to claim 6 wherein said chelating agent is selected from ethylenediaminetetraacetic acid, disodium salt dihydrate, diammonium salt of ethylenediaminetetraacetic acid, tetrasodium ethylene diaminetetraacetic acid, ethylenetriaminepentaacetic acid, phosphonic acid, [(phosphonomethyl)imino]bis[(2,1-ethanediylnitrilo)tetrakis(methylene)] tetrakis-sodium salt, and pentasodium diethylenetriamine pentaacetic acid (DTPA).

8. A clear bar soap composition according to claim 6 wherein said first anionic surfactant is selected from sodium lauryl ether sulfate (SLES), alkyl ether carboxylate, acyl glutamate, amphoacetate, and a combination thereof.

9. A clear bar soap composition according to claim 6 wherein said propylene glycol is from about 8 to about 22% by weight of said composition, said sorbitol is from about 8 to about 16% by weight of said composition, said first anionic surfactant is from about 16 to about 32% by weight of said composition, said glycerin is from about 10 to about 15% by weight of said composition, said water is from about 2 to about 4% by weight of said composition, said stearic acid is from about 13 to about 15% by weight of said composition, said myristic acid is from about 6 to about 7% by weight of said composition, said sodium hydroxide is from about 6 to about 7% by weight of said composition, said chelating agent is from about 0.1 to about 1% by weight of said composition, said SCI is from about 3 to about 6% by weight of said composition, and said one of TEA and ammonium hydroxide is from 0 to about 1.5% by weight of said composition.

10. A clear bar soap composition according to claim 6 further comprising at least one additive selected from a preservative, a dye, a fragrance, a vitamin, a botanical extract, panthenol, a conditioning polymer, a foam stabilizer, a humectant, an antimicrobial agent, and an emollient.

11. A method for producing clear soap bars comprising the steps of:

producing a mixture of propylene glycol, sorbitol, a first anionic surfactant, glycerin, water, stearic acid and myristic acid in a vessel;

heating the mixture while stirring to a temperature from about 45° C. to about 65° C.;

when the mixture is substantially molten, slowly adding NaOH while maintaining a temperature of the mixture from about 65° C. to about 75° C.;

after adding NaOH, stirring until the mixture is substantially homogenized;

adding a quantity of a chelating agent from about 1:1 to about 5:1 by weight ratio to metal catalyst in SCI to the mixture;

after adding the chelating agent, stirring until the mixture is substantially homogenized;

adding a second anionic surfactant, wherein said second anionic surfactant is sodium cocoyl isethionate (SCI) and stirring until the mixture is substantially homogenized and the SCI is dissolved;

adding one of TEA and ammonium hydroxide to the mixture and stirring for a period of about 60 minutes to about 120 minutes;

ceasing said stirring and allowing air bubbles in the mixture to rise to the surface without agitation;

pouring the mixture into molds at a temperature from about 65° C. to about 75° C.; and cooling the mixture undisturbed.

12. A method for producing clear soap bars in accordance with claim 11 wherein said step of adding a chelating agent is performed at a chelating agent quantity from about 0.1 to about 1% by weight.

13. A method for producing clear soap bars in accordance with claim 11 wherein said step of adding said SCI is performed at a temperature from about 65° C. to about 75° C.

14. A method for producing clear soap bars in accordance with claim 11 wherein said step of producing a mixture comprises the step of combining: from about 8 to about 22% by weight of said propylene glycol; from about 8 to about 16% by weight of said sorbitol; from about 16 to about 27% by weight of said first anionic surfactant, from about 10 to about 15% by weight of said glycerin; from about 2 to about 4% by weight of said water; from about 13 to about 15% by weight of said stearic acid; and, from about 6 to about 7% by weight of said myristic acid.

15. A method for producing clear soap bars in accordance with claim 11 wherein said step of producing a mixture further comprises the step of selecting said first anionic surfactant from sodium lauryl ether sulfate (SLES), alkyl ether carboxylate, acyl glutamate, amphoacetate or a combination thereof.

16. A method for producing clear soap bars in accordance with claim 11 wherein said step of adding a chelating agent comprises the step of selecting the chelating agent from ethylenediaminetetraacetic acid, disodium salt dihydrate, diammonium salt of ethylenediaminetetraacetic acid, tetrasodium ethylene diaminetetraacetic acid, ethylenetriaminepentaacetic acid, phosphonic acid, [(phosphonomethyl) imino]bis[(2,1-ethanediylnitrilo)tetrakis(methylene)] tetrakis-sodium salt, and pentasodium diethylenetriamine pentaacetic acid (DTPA).

17. A method for producing clear soap bars in accordance with claim 11 wherein said step of mixing the mixture after adding NaOH is performed for a period of about 30 minutes at a temperature from about 65° C. to about 75° C.

18. A method for producing clear soap bars in accordance with claim 11 wherein said step of stirring the mixture after adding the chelating agent is performed for at least two minutes.

19. A method for producing clear soap bars in accordance with claim 11 wherein said step of adding said SCI and stirring is performed for a period from about 30 minutes to about 60 minutes at a temperature from about 65° C. to about 75° C.

20. A method for producing clear soap bars in accordance with claim 11 wherein said step of allowing air bubbles in the mixture to rise without agitation is performed for a period of about 30 minutes.

* * * * *